United States Patent [19]

Katz

[11] Patent Number: 4,874,794

[45] Date of Patent: Oct. 17, 1989

[54] INFLAMMATORY DISEASE TREATMENT

[75] Inventor: David H. Katz, La Jolla, Calif.

[73] Assignee: Lidak Biopharmaceuticals, La Jolla, Calif.

[21] Appl. No.: 345,084

[22] Filed: Apr. 28, 1989

[51] Int. Cl.$^4$ ............................................ A61V 31/045
[52] U.S. Cl. ..................................................... 514/724
[58] Field of Search ........................................ 514/724

Primary Examiner—Stanley J. Friedman
Attorney, Agent, or Firm—Grant L. Hubbard

[57]  ABSTRACT

A method treating virus-induced and inflammatory diseases of skin and membranes in humans or animals, comprising application of a composition consisting of one or more of the aliphatic alcohols docosanol, tetracosanol and hexacosanol in a physiologically compatible carrier is disclosed.

2 Claims, No Drawings

INFLAMMATORY DISEASE TREATMENT

FIELD OF THE INVENTION

This invention relates to alcohol-containing compositions which are useful in treating virus infections and inflammatory diseases of the skin and membranes, including burns, laceration damage and acute injuries. More specifically the present invention relates to a naarrow class of oaliphatic straightchain saturated monohydric alcohols which have from 20 to 26, preferably 22 to 26, carbons in the chain.

BACKGROUND OF THE INVENTION

It is well-known that certain selected alcohols have some physiological activity. It is known, for example, that 1-triacontanol stimulates the growth of plants, see, e.g. Ries, Stanley K. and Sweeney, Charles C., U.S. Pat. No. 4,150,970. Interestingly, the C-30 aalcohol triacontanol appears to possess this physiologicl activity and that the C-28 and C-32 do not possess such physiological activity, or at least have very much less physiological activity in plant growth, see, e.g., the patents and publications of Ries et al., ibid, and of Ashmead, Harvey H., Weleber, Andrew J., Laughlin, Robert G., Nickey, Donald O. & Parker, Dane. K, and Ohorogge, Alvin J.

Triacontanol has also been reported to accelerate the decomposition of sewage and reduce H.S, Starr, Jerry, U.S. Pat. No. 4,246,100.

Beeswax comprises, inter alia, esters of long-chain aliphatic alcohols having chain lengths in the area of interest, and it is known to obtain such alcohols by hydrolysis of beeswax. Beeswax has been used sicne antiquity in a great variety of cosmetic and thereapeutic applications, as a bse for lipstick, in lotions and creams, as an emollient and as a constituent in therapeutic products for topical and membrane application. Various constituents of beeswax and products derived from beeswax have also been used in cosmetic and therapeutic applications. For example, Slimak, Karen M., U.S. Pat. No. 4,793,991, describes a hypoallerginic cosmetic comprising single plant source beeswax. Gans, Eugen, Nacht, Sergio and Yeung, David have described the use of the non-polar saturated straight chain C-21 to C-33 hydrocarbon fraction of beeswax in the treatment of inflammatory skin disorders, U.S. Pat. No. 4,623,667.

The mechanism of the rather diverse and upredictable physiological effects of the vaarious alcohols are, at best, poorly understood and studies are not generally definitive. There appears to some interaction of certain nalkanols with lipid bilayer membranes, Westerman, PW, Pope, JM, Phonphok, N., Dan, JW, dubro, DW, *Biochim Biophys Acta* (NETHERLANDS) 939, 64–78 (1988), and studies have been conducted respecting the partitioning of long-chain alcohols into lipid bilayers, Franks NP & Lieb WR, *Proc. Natl. Acad. Sci.* USA 83 5116–20 (1986); cholesterol solubility of n-alkanols, Pal S. & Moulik SP, *Indian J Biochem Biophys* 24 24–8 (1987); neurological effects of certain long-chain alcohols, Natarajan V & Schmid HH, *Lipids* 12 128–30 (1977); Snider SR, *Ann Neurol* 16 723 (1984); Borg J, Toazara J. Hietter H, Henry M, Schmitt G, Luu B, *FEBS Lett* 213 406–10 (1987).

Levin, Ezra reported that tetracosanol, hexacosanol, octacosanol and triacontanol aand their esters improved physical performance of athletes and disclosed compositions comprising such alcohols and esters in vegetable oil bases for oral ingestion, U.S. Pat. No. 3,031,376.

An incidental disclosure of a composition intended for topical application comprising a major portion liquified gaseous propellant and a minor portion of a mixiture of C-12 to C-30 fatty alcohols which were used simply to mark the areas of application of the aerosol is contained in U.S. Pat. No. 3,584,115 to Gebhart.

Clark, U.S. Pat. No. 4,670,471 discloses the use of triacontanol, in a suitable carrier, as a treatment for inflammatory disorders such as herpes simplex, eczema, shingles, atopic dermatitis, psoriasis, etc. Clark performed experiments with the compositions of the type disclosed by Gebhart, U.S. Pat. No. 3,584,115 comprising an aerosol and a mixture of triacontanol and palmitic acid, which Clark indicates to be as effective as pure triacontanol, and concluded that the aerosol carrier destroyed the effect of triacontanol and that a hydrophilic carrier for triacontanol was necessary to achieve the desired anti-inflammatory effect. There is some reason to believe that Clark's composition was simply saponified beeswax which would contain triacontanol and palmitic acid, as Clark indicates, but which would also contain, as substantial constituents, hexacosanolic acid nd various hydrocarbons. Results of gas chromatographic-mass spectrum analysis of various compositions believed to have been used by Clark were not definitive, but suggested that at least some such compositions were very complex mixtures, some of which may be lower alkanes, esters, acids or alcohols. Whether or not these were found by Clark to be effective anti-inflammatory compositions is not known. McKeough, Mark & Spruance, SL evaluated the efficacy of 5 percent triacontanol in a branch chain ester base in the treatment of HSV-1 dorsal cutaneous infection in guinea pigs and concluded that the active ingredient in triacontanol is the long chain hydrocarbon (unpublished report in the file of U.S. Pat. No. 4,670,471).

Revici, Emanuel, Sherwood, Bob E., Benecke, Herman P., Rice, John M., and Geisler, Richard W., U.S. Pat. No. 4,513,008, disclose a method of inactivating developed virus using C-20 to C-24 polyunsaturated acids, aldehydes or alcohols having 5–7 double bonds, and references disclosures by Sands et al. (*Antimicrobial Agents and Chemotherapy* 15, 67–73 (1979)), antiviral acivity of C-14 to C-20 unsaturated alcohols having 1–4 double bonds, C-20 tetraenyl alcohol having low activity, Snipes et al., (*Antimicrobial Agents and Chemotherapy* 11, 98–104 (1977) and *Symp. Pharm. Effects Lipids* (*AOCS Monograph No.* 5) 63–74 (1978) even lower antiviral activity for saturated long-chain alcohols.

Katz, Martin & Neiman, Herbert M, U.S. Pat. No. 3,592,930 disclose a medicant vehicle containing from 15 to 45 parts of saturated fatty alcohol from 16 to 24 carbons, along with glycol solvent, plasticizer, penetrant and adjuvant which is used as a carrier for oantibiotics, steriods, antihistamines, etc.

Ryde, Emma Marta & Ekstedt, Jan Erik, U.S. Pat. No. 3,863,633 disclose a composition for topical treatament of the eye which comprises a lipophilic substance, a hydrophilic swellable polymer and from 10 to 80 percent C-12 to C-22 surface active alcohols such as 1-docossanol, 1-hexadecanol, 1-octadecanol and 1-eicosanol which serve as a stabilizer for the mixture.

The content of othe prior art and the corresponding skill of the art, relative to topically administered compositions, may be summarized as follows: Short-chain alcohols, i.e. under about 16 carbons, tend to be irritants while longer chain alcohols, particularly the aliphatic alcohols tend to be non-irritating (Katz et al., supra). 1-Triacontanol, a 30-carbon unsaturated aliphatic alcohol, in a suitable hydrophilic carrier has (or may have depending upon the precise compositions used by Clark) value in treating inflammatory conditions of the skin (Clark, supra). Shorter chain C-10 to C-14 aliphatic alcohols demonstrate low level in vitro virucidal characteristics, while C-18 alcohols show noo discernable virucidal activity in vitro (Snipes, supra). Polyunsaturated C-20 to C-24 alcohols inactive enveloped virus (Revici et al., supra). C-16 to C-24 aliphatic alcohols are useful as stabilizers in carrier compositions for drugs having diverse physiological activity.

Respecting aliphatic alcohols, one would predict from the studies of Snipes and Clark that, in the continuum of aliphatic alcohols from C-10 to C-30 virucidal activity, at a very low level, may appear (if in vitro studies may be used to predict in vivo results) in C-10 to C-14 alcohols (which would also be irritants as reported by Katz), that virucidal activity disappears inthe C-16 to C-28 range and than appears uniquely (if Clark's compositions were pure triacontanol or mixtures of triacontanol with palmitic acid as he indicates) with the C-30 alcohol 1-triacontanol, which has been shown to have unique physiological effects in plant treatment.

Even considering the possible ambiguity of Clark's compositions, one would not predict any significant virucidal activity for aliphatic alcohols in the C-20 through C-28 chain-length.

Notwithstanding the negative teachings of the prior art, the present invention comprises compositions and methods for topical treatment of inflammatory diseases, including virus-induced inflammation, burns, laceration damage and acute injuries, in which the active constitute consists essentially of C-20 to C-26, and preferably C-22 to C-26 aliphatic alcohols, e.g. docosanol, tetraccosanol and hexacosanol.

SUMMARY OF THE INVENTION

The present invention is embodied in a method treating inflammatory and viral skin diseases, such as may result, for example, from virus infection, burns, lacerations and acute injuries, comprising application of a composition consisting of one or more of C-20 to C-26 aliphatic alcohols, preferably one or more alcohols selected from the group consisting of 1-docosanol, 1-tetracosanol and 1-hexacosanol in a physiologically compatible carrier.

DESCRIPTION OF THE PREFERRED EMBODIMENTS

The compositions suitable for use in this invention consists essentially of a carrier which is physiologically compatible with the skin and membrane tissues of the patient, i.e. non-irritating, and which is substantially inactive physiologically (except for possible emollient properties) and, as the physiologically active composition, one or more C-20 to C-26 aliphatic alcohols, e.g. one or more of 1-eiconol, 1-docosanol, 1-tetracosanol and 1-hexacosanol.

The method may be carried out using compositions inwhich the sole physiologically active agent(s) is the C-20 to C-26 aliphatic alcohol, or comparable compositions which may also include other physiologically active constituents which do not interfere with the efficacy of the C-20 to C-26 alcohols.

The composition of the carrier is not critical so long as the carrier is non-irritating to skin and membranes and is substanatially free from physiological effect, e.g. has no physiological effect other than be an emollient.

An exemplary composition for use in this invention would be similar to that disclosed by Katz, et al. in U.S. Pat. No. 3,592,930 without the addition of any other physiologically active constituent, e.g. a mixture of C-20 to C-26 alcohols, preferably one or more of the alcohols 1-docosanol, 1-tetracosanol and 1-hexacosanol, a glycol solvent such as propylene glycol, and, if desired, a plasaticizer such as glycerol or a polyethylene glycol having a molecular weight of from 800 to 20,000.

A suitable carrier may comprise white petrolatum, stearyl alcohol, isopropyl myristate, sorbitan monooleate, propylelne glycol, water and a detergent such as polyoxyl stearate mixed for form a stable cream. The active alcohols, e.g. one or more of 1-docosanol, 1-tetracosanol and 1-hexacosanol is added to the carrier in amounts from about 0.1 to about 25 percent by weight, typically in the range of from 1 to 5 percent. Higher concentrations of the active alcohol(s) may be used but no increase in efficacy results from concentrations above about 15 to 25 weight percent. The concentration of the active alcohol(s) is not critical, but optimum efficacy coupled with efficient use of the active ingredient would be found in the 1 to 5 weight percent range.

Another suitable composition for use in the method of this invention would be a cream formulated of water, white petrolatm, isopropyl myristate, lanolin alcohols, mineral oil and cetylstearyl alcohol into which from 1 to 5 percent of C-20 to C-26 alcohols, e.g. one or more alcohols selected from the group consisting of 1-docosanol, 1-tetracosanol and 1-hexacosanol has been intimately mixed.

An alternative suitable composition for use in this invention may be formulated of stearyl alcohol, petrolatum, water and mineral oil stabilized with a detergent such as sodium lauryl sulfate and may include a preservative such as methylparaben or propylparaben, and an effective amount, typically from about 0.1 to 5 percent by weight of one or more alcohols selected from the group consisting of 1-docosanol, 1-tetracosanol and 1-hexacosanol.

In all cases, suitale preservatives, such as ethylene diamine tetraacetate salts, methylparaben, propylparaben, etc., may be added to prevent bacterial and fungal growth. Penetrants, such as a zone, may also be added if desired.

The method of the present invention will require application to the inflamed area of skin or membrane of compositions, such as those described above as merely exemplary, in which the active ingredient consists essentially of one or more aliphatic alcohols having from 20 to 26 carbons in the aliphatic chain, an exemplary composition comprising one or more alcohols selected from the group consisting of 1-docosanol, 1-tetracosanol and 1-hexacosanol. Three to 6 appliccations of the ointment or ocream per day will, in most cases, be expected to produce prompt relief from the itching, discomfort associated with such diseases and promote healing of damaged tissues within a few days to a few weeks.

The method described is useful in treating a wide variety of viral and inflammatory diseases, examples of which include herpes, simplex, eczema, shingles psoriasis, atopic dermatitis, and in treating inflammation resulting from burns, lacerations and acute injuries.

It will be readily understood from the foregoing that the essential constituent(s) of the compositions useful in the present method is one or more aliphatic alcohols having from 20 to 26 carbons in the aliphatic chain of the alcohol(s), and that the composition of the carrier is non-critical and subject to great variation.

INDUSTRIAL APPLICATION

This invention is useful in treating virus-induced inflammatory diseases of humans and other animals, and inflammation resulting from burns, lacerations and acute injuries.

What is claimed is:

1. A method treating virus-induced and inflammatory diseases of skin and membranes in humans or animals, comprising topical application of a composition consisting of one or more of the aliphatic alcohols docosanol, tetracosanol and hexacosanol in a concentrration of from 0.1 to 25 percent by weight in a physiologically compatible carrier to the inflalmed skin or membrane of the patient to be treated.

2. The method of claim 1 wherein said alcohols are in a concentration of from about 1 to about 5 percent.

* * * * *

UNITED STATES PATENT AND TRADEMARK OFFICE

(12)      CERTIFICATE EXTENDING PATENT TERM
UNDER 35 U.S.C. § 156

| | | | |
|---|---|---|---|
| (68) | PATENT NO. | : | 4,874,794 |
| (45) | ISSUED | : | October 17, 1989 |
| (75) | INVENTOR | : | David H. Katz |
| (73) | PATENT OWNER | : | AVANIR PHARMACEUTICALS |
| (95) | PRODUCT | : | ABREVA® (docosanol) |

This is to certify that an application under 35 U.S.C. § 156 has been filed in the United States Patent and Trademark Office, requesting extension of the term of U.S. Patent No. 4,874,794 based upon the regulatory review of the product ABREVA® (docosanol) by the Food and Drug Administration. Since it appears that the requirements of the law have been met, this certificate extends the term of the patent for the period of

(94)                   Five years from April 28, 2009, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 3rd day of April 2003.

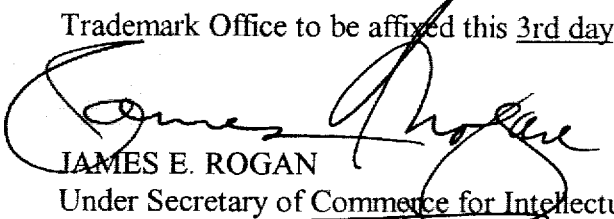

JAMES E. ROGAN
Under Secretary of Commerce for Intellectual Property and
Director of the United States Patent and Trademark Office